United States Patent [19]

Kanga et al.

[11] Patent Number: 5,798,111
[45] Date of Patent: Aug. 25, 1998

[54] CLEAR EMULSION COSMETIC COMPOSITIONS

[75] Inventors: Vispi Dorab Kanga, Shelton; Craig Stephen Slavtcheff, Guilford; Alexander Paul Znaiden, Trumbull, all of Conn.

[73] Assignee: Chesebrough-Pond's USA Co., Division of Conopco, Inc., Greenwich, Conn.

[21] Appl. No.: 884,303

[22] Filed: Jun. 27, 1997

[51] Int. Cl.$^6$ .................................................. A61K 7/02
[52] U.S. Cl. .......................... 424/401; 514/844; 514/937
[58] Field of Search .......................... 424/401, 78.03; 514/844, 937

[56] References Cited

U.S. PATENT DOCUMENTS

| | | | |
|---|---|---|---|
| 4,806,572 | 2/1989 | Kellett | 521/112 |
| 4,886,545 | 12/1989 | Peck et al. | 71/88 |
| 5,011,681 | 4/1991 | Ciotti et al. | 424/81 |
| 5,160,739 | 11/1992 | Kanga | 424/401 |
| 5,216,033 | 6/1993 | Pereira et al. | 514/844 |
| 5,302,382 | 4/1994 | Kasprzak | 424/78.03 |
| 5,306,838 | 4/1994 | Shioya et alk. | 556/445 |
| 5,332,569 | 7/1994 | Wood et al. | 424/70 |
| 5,340,570 | 8/1994 | Wong et al. | 424/71 |
| 5,387,417 | 2/1995 | Rentsch | 424/401 |
| 5,439,682 | 8/1995 | Wivell et al. | 724/401 |
| 5,456,915 | 10/1995 | Nagase et al. | 424/401 |
| 5,525,344 | 6/1996 | Wivell | 424/401 |

FOREIGN PATENT DOCUMENTS

97/14398  4/1997  WIPO .

OTHER PUBLICATIONS

MP Diol Glycol: A New Raw Material for Personal Care, DCI Mar. 1997, pp. 30–32.
Photocopy of Oil of Olay Moisturizing Body Wash Bottle–1992.
Photocopy of Ponds Cold Cream Water Rinsable Cleanser Carton–1995.
Photocopy of Oil Olay Water Rinsable Cold Cream Carton–1995.
Chemical & Engineering News Jul. 1, 1996, vol. 74, No. 27, pp. 13–19.

*Primary Examiner*—Thurman K. Page
*Assistant Examiner*—James M. Spear
*Attorney, Agent, or Firm*—Milton L. Honig

[57] ABSTRACT

Clear emulsion cosmetic compositions are provided that include an aqueous phase having 2-methyl-1,3-propanediol and an oily phase containing silicones, especially cyclomethicone and a cyclomethicone-dimethicone copolyol silicone fluid mixture. These compositions exhibit visual clarity and can be formulated into a cold cream or antiperspirant/deodorant which are highly phase stable and insensitive to shear decomposition while being processed.

6 Claims, No Drawings

5,798,111

CLEAR EMULSION COSMETIC COMPOSITIONS

BACKGROUND OF THE INVENTION

1. Field of the Invention

The invention concerns cosmetic emulsion compositions, especially semi-solid gels such as non-classical cold creams that are clear and exhibit improved phase stability and make-up removal efficacy.

2. The Related Art

Modern cleansing creams are based on the solvent action of mineral oil to remove through binding either grime or make-up from skin. Removal of pigments of rouge, lipstick and face powder is a daily problem for most women. Cleansing creams have proved the ideal agent to perform this function.

Historically cleansing creams evolved over a period of centuries. Galen, a Greek physician around the year 150, is reported to be the inventor of the first cold cream. Skin preparations of that period consisted of animal and vegetable fats and oils. Beeswax and olive oil were the prime ingredients. Galen conceived the idea of incorporating water into a molten mixture of beeswax and olive oils. In the resultant product, the emollient effect of oil was accelerated, and a pleasant cooling effect was obtained from evaporation of water. Unfortunately the process of manufacture was slow and laborious. Products were also unstable and subject to developing rancidity. In time, sweet almond oil replaced the olive oil of the older formulations. Borax was introduced to cut manufacturing time, and a whiter and more stable emulsion resulted.

A cold cream can be classified as a form of cleansing cream but with a heavier body. These products were originally described as "refrigerans", latin for "making cold", because when applied they create a cooling sensation. Until early this century, many druggists would compound their own Ointment of Rose Water and keep it fresh on ice, hence, "cold" skin cream. The dictionary describes cold cream as a soothing and cleansing cosmetic or a cosmetic, typically of oily and heavy consistency, used to soothe and cleanse the skin. Classic cold cream is one containing the components beeswax, mineral oil, water and borax. Interest has arisen in non-classical forms of cold cream, especially those that combine enhanced aesthetics with efficacy.

U.S. Pat. No. 5,525,344 (Wivell) discloses a clear cold cream of improved make-up removal efficacy. The cold cream is a combination of volatile $C_{10}$–$C_{20}$ hydrocarbon in an aqueous emulsion with a $C_2$–$C_6$ polyhydric alcohol, a poly ($C_2$–$C_4$ alkoxylate) polymer and a silicone oil emollient system.

Despite such advances in the art, there remains a need for higher performance products. While the Wivell system is good, there is need for improving viscosity stability and eliminating sensitivity to shear stress during processing. Improved make-up removal is a further goal.

Accordingly, it is an object of the present invention to provide a cosmetic composition which is a clear (transparent) product retaining many of the physical attributes of the traditional opaque cold creams.

It is another object of the present invention to provide a cosmetic composition having superior skinfeel (non-greasy) and grease, make-up removal and cleansing efficacy comparable to traditional cold cream.

A still further object of the present invention is to provide a cosmetic composition in emulsion form having good viscosity stability and processability.

These and other objects of the present invention will become more readily apparent through the following summary and detailed description.

SUMMARY OF THE INVENTION

A clear emulsion cosmetic composition is provided that includes:

(i) from 10 to 97% by weight of an aqueous phase comprising 2-methy-1,3-propanediol; and (ii) from 2 to 90% by weight of an oily phase including a silicone oil.

DETAILED DESCRIPTION OF THE INVENTION

It has been discovered that a clear semi-solid composition can be obtained having stable viscosity, improved processability and when used as a cold cream has improved make-up removal/cleansing efficacy. The composition is a water and oil emulsion containing in the aqueous phase 2-methyl-1,3-propanediol and in the oily phase one or more silicone oils.

Compositions of the present invention may be water-in-oil or oil-in-water or even duplex emulsions. Amounts of the aqueous phase of the emulsion will range from 10 to 97%, preferably from 40 to 90%, optimally between 55 and 85% by weight. Amounts of water in the aqueous phase may range from 1 to 90%, preferably from 20 to 80%, optimally from 40 to 70% by weight. The oily phase of the emulsion will constitute from 2 to 90%, preferably from 5 to 60%, optimally from 10 to 40% by weight.

Compositions of the present invention are intended to be optically clear cosmetic products with the ability to be transparent when packaged in a clear container. These compositions may preferably have a refractive index of 1.3975 to 1.4200 at 21° C., an optical clarity better than 50 NTU (Nephelometric Turbidity Units) at 21° C. and a viscosity of at least 10,000 cps, preferably at least 30,000 cps at 21° C. The refractive indices (measured at 5891° A) of the water and oil phases should match within 0.0050, preferably within 0.0004 refractive index units. An optically clear composition of the present invention should be one that is visually clear, and like glass, allows ready viewing of objects behind it. Preferably, the compositions will have a turbidity measurement of less than 30 NTU. Distilled water has a turbidity of 1 NTU and whole milk diluted 1 part in 350 parts of distilled water has a turbidity of 200 NTU.

An essential element of the aqueous phase will be the presence of 2-methyl-1,3-propanediol, commercially available under the trademark MP Diol glycol from the Arco Chemical Company. Amounts of this diol will range from 1 to 70%, preferably from 10 to 50%, optimally from 20 to 40% by weight of the cosmetic composition. Other than water, this diol preferably is the component of highest concentration in the aqueous phase, and even in the total cosmetic composition.

Other polyhydric alcohols may be employed as adjunct in the aqueous phase. These polyhydric alcohols may contain from 2 to 6 hydroxyl groups, preferably from 2 to 3 hydroxyl groups. They may also contain from 2 to 6 carbon atoms, preferably from 2 to 3 carbon atoms. Suitable polyhydric alcohols include ethylene glycol, propylene glycol, trimethylene glycol, glycerin and sorbitol. Most preferred is glycerin. Amounts of the polyhydric alcohol may range from 1 to 30%, preferably from 2 to 25%, optimally from 5 to 12% by weight of the cosmetic composition.

A further possible component of the aqueous phase of compositions according to the present invention is that of a poly ($C_2$–$C_4$ alkoxylate) polymer. This polymer will contain from 3 to 200 units of $C_2$–$C_4$ alkylene oxide monomer units. These units may either be homopolymerized, copolymerized with another alkylene oxide monomer unit, or condensed with an organic hydrophobe such as a $C_2$–$C_{20}$ alkanoic acid or alcohol. Illustrative homo- and co-polymers are polyethylene glycol, polypropylene glycol and poly(ethylene oxide) (propylene oxide) (commercially available from the BASF Corporation under the Pluronic trademark). Illustrative of those with hydrophobe units are PPG-15 stearyl ether, PEG-10 stearyl ether, PPG-15 palmityl ether and Poloxamine 1307 (commercially available from the BASF Corporation under the Tetronic® 1307 trademark). Most preferred is polyethylene glycol, especially PEG 5, PEG 32, PEG 400, PEG 540, PEG 600 and combinations thereof. Most preferred is PEG 600, sold by the Union Carbide Corporation and having 12 moles of ethylene glycol per polymer chain. Amounts of the poly ($C_2$–$C_4$ alkoxylate) polymer will range from 1% to 45%, preferably from 10 to 30%, optimally from 15 to 25% by weight of the cosmetic composition.

Nonionic surfactants may also be included in compositions of this invention. Most preferred are the alkyl polyglycosides such as Planteren 2000 (decyl polyglucose) available from the Henkel Corporation. Amounts of the nonionic surfactant may range from 0.5 to 20%, preferably from 1 to 10%, optimally from 1.5 to 5% by weight of the cosmetic composition.

Preservatives can also be incorporated in amounts effective to protect against growth of potentially harmful microorganisms. Preferably they are added to the aqueous phase, but some may be added to the oil phase. Levels of such preservatives may range from about 0.001 to about 1% by weight. Illustrative preservatives are methyl paraben, propyl paraben, imidazolidinyl urea, sodium dehydroxyacetate and benzyl alcohol.

Other minor adjunct ingredients may also be included such as fragrances, electrolytes and colorants, each in effective amounts to accomplish their respective function.

The oily phase of emulsion compositions according to the present invention will comprise at least one silicone oil. Silicone oils will constitute from 2 to 70%, preferably from 3 to 50%, optimally from 5 to 15% by weight of the cosmetic composition. These silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9 and preferably from 4 to 5 silicone atoms. The linear types are known by the CTFA name dimethicone while the cyclic types are known by the CTFA name of cyclomethicone. The cyclomethicones are commercially available from Dow Corning under the trademark DC 244, DC 245, DC 344 and DC 345.

Nonvolatile silicone oils useful in compositions of the present invention are exemplified by the polyalkyl siloxanes, polyalkyaryl siloxanes and polyether siloxane copolymers. The essentially nonvolatile polyalkyl siloxanes useful herein include, for example, polydimethyl siloxanes with viscosities of from 5 to 100,000 centistokes at 25° C. Preferred polydimethyl siloxanes are those having viscosities from 10 to 400 centistokes at 25° C. Such polyalkyl siloxanes include the Viscasil series (sold by General Electric Company) and the Dow Corning 200 series (sold by Dow Corning Corporation). Polyalkylaryl siloxanes include poly (methylphenyl)siloxanes having viscosities of from 15 to 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of 1200 to 1500 centistokes at 25° C. Such a fluid is available as SF-1066 organosilicone surfactant (sold by General Electric Company).

For purposes of this invention, most advantageous is the use of a combination of cyclomethicone, dimethicone copolyol and dimethiconol. In particular, it is desirable to use a combination of DC 3225C and DC 1401 in combination with cyclomethicone (e.g. DC 344). Dow Corning 3225C is a mixture cyclomethicone-dimethicone copolyol silicone fluid having a viscosity at 25° C. of 100–1,000 cst and a specific gravity at 25° C. of 0.963. Amounts of this particular silicone will be present from 1 to 50%, preferably from 3 to 15% by weight of the cosmetic composition. Dow Corning 1401 is a blend of cyclomethicone and dimethiconol having a viscosity at 25° C. of 4,000–7,000 cst and a specific gravity at 25° C. of 0.960. Amounts of DC 1401 may range from 0.5 to 10%, preferably from 1 to 5% by weight of the total composition.

Other adjunct functional ingredients may be incorporated into the oil phase. For instance, cold cream compositions may utilize from 0.1 to 15% by weight of a hydrocarbon. For instance, the hydrocarbon may be a Permethyl 99A or 101; preferably it is a hydrogenated polyisobutene such as Panalane L-14E available from Lipo Chemical Company. Fragrances and sunscreens, such as Parsol 1789 and Parsol MCX, may be included at levels ranging from 0.01 to 1.5% by weight of the cosmetic composition.

While the present invention is primarily concerned with clear cold creams, the invention is also applicable to clear deodorant and antiperspirant compositions. These compositions will require the further presence of an astringent metal salt such as aluminum chlorohydrate, activated aluminum chlorohydrate and aluminum-zirconium tetrachlorohydrexglycine and related salts. Amounts of the astringent salt may range from 5 to 40% by weight of the cosmetic composition. Deodorant actives besides astringent salts include zinc oxide, triclosan and tricloban. Amounts of these materials may range from 0.1 to 15% by weight of the cosmetic composition.

The following examples will more fully illustrate select embodiments of this invention. All parts, percentages and proportions referred to here and in the appended claims are by weight unless otherwise indicated.

EXAMPLES 1–10

A series of cold cream compositions according to the present invention are described below.

TABLE I

| COMPONENT | EXAMPLE | | | | | | | | | |
|---|---|---|---|---|---|---|---|---|---|---|
| | 1 | 2 | 3 | 4 | 5 | 6 | 7 | 8 | 9 | 10 |
| PHASE A | | | | | | | | | | |
| Witch Hazel Extract | 20.00 | 20.00 | — | — | — | — | 10.00 | 10.00 | 10.00 | 10.00 |
| Tetrasodium EDTA | 0.02 | 0.02 | 0.02 | 0.02 | 0.02 | 0.02 | 0.02 | 0.02 | 0.02 | 0.02 |
| Sodium Chloride | 3.00 | 2.00 | 1.00 | 3.00 | 3.00 | 3.00 | 2.00 | 2.00 | 3.00 | 3.00 |

TABLE I-continued

| COMPONENT | EXAMPLE | | | | | | | | | |
|---|---|---|---|---|---|---|---|---|---|---|
| | 1 | 2 | 3 | 4 | 5 | 6 | 7 | 8 | 9 | 10 |
| Glycerin | 5.00 | 5.00 | 6.00 | 7.00 | 7.00 | 8.00 | 8.00 | 5.00 | 5.00 | 5.00 |
| Diglycerin | 5.00 | 5.00 | 6.00 | — | — | — | — | 5.00 | 5.00 | 5.00 |
| Isoprene Glycol ® | — | — | — | — | — | — | 5.00 | 5.00 | 5.00 | 5.00 |
| MP Diol Glycol ® | 25.00 | 25.00 | 30.00 | 30.00 | 15.00 | 35.00 | 40.00 | 40.00 | 40.00 | 40.00 |
| 1,3-Butanediol | — | — | — | — | — | 5.00 | — | — | — | — |
| PEG-540 Blend ® | 3.50 | 3.50 | — | — | 2.00 | 2.00 | 2.00 | — | — | — |
| PEG-600 Blend ® | — | — | 2.00 | 3.50 | 3.50 | 2.00 | 2.00 | — | — | — |
| Planteren 2000 ® | 1.00 | 1.00 | 1.50 | 3.50 | 3.50 | 2.00 | 2.00 | — | — | — |
| DL Panthenol | 0.01 | 0.01 | 0.01 | 0.01 | 0.01 | 0.01 | 0.01 | 0.01 | 0.01 | 0.01 |
| Glycolic Acid | 0.50 | — | 2.00 | — | — | — | — | — | — | — |
| Benzyl Alcohol | 0.50 | 0.50 | 0.50 | 0.50 | 0.50 | 0.50 | 0.50 | 0.50 | 0.50 | 0.50 |
| Phenoxyethanol/Parabens | 0.20 | 0.20 | 0.20 | 0.20 | 0.20 | 0.20 | 0.20 | 0.20 | 0.20 | 0.20 |
| Colorant | 0.03 | 0.03 | 0.03 | 0.03 | 0.03 | 0.03 | 0.03 | 0.03 | 0.03 | 0.03 |
| Water | qs | qs | qs | qs | qs | qs | qs | qs | qs | qs |
| PHASE B | | | | | | | | | | |
| Panalane L-14E ® | — | — | — | 3.00 | 3.00 | 3.00 | 3.00 | 1.50 | 1.50 | 1.50 |
| Permethyl 99A ® | 3.00 | 3.00 | 3.00 | — | — | — | — | 1.50 | 1.50 | 1.50 |
| DC 1401 Fluid ® | 0.50 | 0.50 | 1.00 | 1.50 | 2.00 | 3.00 | 1.50 | 1.50 | 1.50 | 1.50 |
| DC 344 Fluid ® | 9.87 | 9.87 | 6.00 | 9.37 | 12.37 | 8.37 | 7.50 | 7.50 | 7.50 | 7.50 |
| DC 3225C ® | 10.00 | 9.00 | 8.00 | 8.00 | 8.00 | 7.00 | 5.00 | 5.00 | 5.00 | 5.00 |
| Fragrance | 0.14 | 0.14 | 0.14 | 0.14 | 0.14 | 0.14 | 0.14 | 0.14 | 0.14 | 0.14 |
| Parsol 1789 ® | 0.03 | — | — | 0.03 | 0.03 | — | — | — | — | — |

EXAMPLE 11

A series of performance experiments were conducted to establish the special usefulness of 2-methyl-1,3-propanediol (MP diol glycol) for cold cream compositions. Five creams were prepared all identical except each contained 30% of a different polyhydric diol. These creams are outlined in Table II below.

Table III describes the clarity of each of the above samples both initially and under 50° C. storage conditions for two weeks (measured at room temperature and hot). Clarity rating was on a scale from 1.0 (clear transparent) down to 5.0 (whitish opaque). Only Sample A resulted in a clear transparent material directly after manufacture, measured at room temperature. After storage at 50° C. for two

TABLE II

Cream Formulas

| COMPONENT | SAMPLE A | SAMPLE B | SAMPLE C | SAMPLE D | SAMPLE E |
|---|---|---|---|---|---|
| WATER PHASE | WEIGHT % | | | | |
| Water | 29.85 | 29.85 | 29.85 | 29.85 | 29.85 |
| Tetrasodium EDTA | 0.02 | 0.02 | 0.02 | 0.02 | 0.02 |
| Witch Hazel | 0.20 | 0.20 | 0.20 | 0.20 | 0.20 |
| Sodium Chloride | 3.00 | 3.00 | 3.00 | 3.00 | 3.00 |
| MP Diol Glycol | 30.00 | — | — | — | — |
| Glycerin | 7.00 | 37.00 | 7.00 | 7.00 | 7.00 |
| Polyethylene Glycol 400 | — | — | 30.00 | — | — |
| Propylene Glycol | — | — | — | 30.00 | — |
| 1,3 Butanediol | — | — | — | — | 30.00 |
| PEG 600 | 3.50 | 3.50 | 3.50 | 3.50 | 3.50 |
| DL Panthenol | 0.10 | 0.10 | 0.10 | 0.10 | 0.10 |
| Benzyl alcohol | 0.50 | 0.50 | 0.50 | 0.50 | 0.50 |
| Phenonip | 0.20 | 0.20 | 0.20 | 0.20 | 0.20 |
| Plantaren 2000 ® | 3.50 | 3.50 | 3.50 | 3.50 | 3.50 |
| Colorant | 0.03 | 0.03 | 0.03 | 0.03 | 0.03 |
| OIL PHASE | | | | | |
| Parsol 1789 ® | 0.03 | 0.03 | 0.03 | 0.03 | 0.03 |
| Panalene L-14E ® | 3.00 | 3.00 | 3.00 | 3.00 | 3.00 |
| Permethyl 99A ® | 0.05 | 0.05 | 0.05 | 0.05 | 0.05 |
| DC 1401 Fluid ® | 1.50 | 1.50 | 1.50 | 1.50 | 1.50 |
| DC344 Fluid ® | 9.37 | 9.37 | 9.37 | 9.37 | 9.37 |
| DC 3225 C ® | 8.00 | 8.00 | 8.00 | 8.00 | 8.00 |
| Vitamin E Acetate | 0.01 | 0.01 | 0.01 | 0.01 | 0.01 |
| Fragrance | 0.14 | 0.14 | 0.14 | 0.14 | 0.14 | weeks, Sample A still remained clear while the other samples did not improve in clarity.

TABLE III

| Sample | Initial Clarity (Room Temperature Measurement) | Clarity After 50° C. Storage For 2 Weeks (Room Temperature Measurement) | Clarity After 50° C. Storage For 2 Weeks (Hot Measurement) |
| --- | --- | --- | --- |
| A | Clear (5.0) | Clear (5.0) | Clear |
| B | Hazy/Whitish (2.0) | Opaque/Whitish (2.0) | Opaque/Whitish |
| C | Hazy, Whitish (2.0) | Opaque/Whitish (2.0) | Opaque/Whitish |
| D | Translucent to Hazy (3.0) | Translucent to Hazy (3.0) | Clear |
| E | Translucent (4.0) | Translucent/Hazy (4.0) | Translucent/Hazy |

Color cosmetic removal performance tests were performed on Samples A through E. Ten panelists were involved in the comparative tests. Under Test 1, panelists treated one area of their skin with Sample A while another was treated with an equal amount of Sample B. Each area was rubbed in a uniform manner to remove the mascara. Panelists were requested to rate removal efficiency on a scale from 1.0 to 5.0, the 1.0 being no removal while the 5.0 reflected complete removal of color cosmetic. Tests 2, 3 and 4 repeated the procedure with Sample A being compared respectively to Samples C, D and E. A series of similar tests were performed substituting make-up on cheek areas for the mascara.

Table IV lists results of the color cosmetic removal tests. Values entered under mascara and make-up list the number of panelists reporting better performance for one sample over another. For instance, Test 1 found that 10 panelists favored Sample A while none favored Sample B. Similar favorable comparisons were found against the Samples C, D and E for both mascara and make-up removal. In all instances, Sample A received a rating of 5.0 (complete removal) in all evaluations. Ratings for the other samples ranged from 1.0 to 4.0, with but two exceptions. One of the panelists in Tests 3 and 4 scored both Samples as equivalent, each as a 5.0. All other evaluations and ratings favored Sample A, most had a difference of at least 2.0 rating points.

TABLE IV

| TEST | SAMPLE | ARDEN ® MASCARA | ARDEN ® MAKE-UP |
| --- | --- | --- | --- |
| 1 | A | 10 | 10 |
|   | B | 0 | 0 |
| 2 | A | 10 | 10 |
|   | C | 0 | 0 |
| 3 | A | 10 | 9* |
|   | D | 0 | 0 |
| 4 | A | 10 | 8* |
|   | E | 0 | 0 |

*Tenth panelist scored both samples as equivalent, each as a 5.0.

EXAMPLES 12–20

A series of antiperspirant and deodorant compositions within the context of the present invention are described in Table V.

TABLE V

| COMPONENT | 12 | 13 | 14 | 15 | 16 | 17 | 18 | 19 | 20 |
| --- | --- | --- | --- | --- | --- | --- | --- | --- | --- |
| PHASE A |   |   |   |   |   |   |   |   |   |
| Aluminum Chlorohydrate | 30.00 | — | — | 35.00 | 35.00 | — | — | — | — |
| Aluminum Zirconium Tetrachlorohydrex—Gly | — | 20.00 | 25.00 | — | — | 25.00 | 25.00 | — | — |
| MP Diol Glycol | 15.00 | 20.00 | 20.00 | 20.00 | 20.00 | 15.00 | 20.00 | 30.00 | 30.00 |
| Ethanol | 5.00 | — | — | 5.00 | 5.00 | — | — | — | 5.00 |
| Propylene Glycol | — | 5.00 | 5.00 | — | — | — | — | — | 10.00 |
| Water | qs | qs | qs | qs | qs | qs | qs | qs | qs |
| PHASE B |   |   |   |   |   |   |   |   |   |
| DC 244 | 10.00 | — | — | 10.00 | 10.00 | 10.00 | 10.00 | — | — |
| DC 344 | — | 10.00 | 10.00 | 5.00 | 5.00 | — | — | 8.00 | 8.00 |
| DC 1401 | 2.00 | 2.00 | 2.00 | 2.00 | 1.50 | 1.00 | 1.00 | 2.00 | 2.00 |
| DC 3225C | 20.00 | 25.00 | 20.00 | 10.00 | 15.00 | 20.00 | 20.00 | 30.00 | 30.00 |
| Fragrance | 0.30 | 0.30 | 0.30 | 0.30 | 0.30 | 0.30 | 0.30 | 0.30 | 0.30 |
| Triclosan | — | — | — | — | — | — | — | — | 0.25 |
| Tricloban | — | — | — | — | — | — | — | 0.25 | — |

The foregoing description and examples illustrate selected embodiments of the present invention. In light thereof variations and modifications will be suggested to one skilled in the art, all of which are within the spirit and purview of this invention.

What is claimed is:

1. A clear emulsion cosmetic composition having an optical clarity of better than 50 NTU at 21° C. comprising:
   (i) from 10 to 97% by weight of an aqueous phase comprising 2-methyl-1,3-propanediol; and
   (ii) from 2 to 90% by weight of an oily phase comprising a silicone oil.

2. The composition according to claim 1 wherein the silicone oil comprises from 1 to 50% by weight of the cosmetic composition of a cyclomethicone-dimethicone copolyol silicone fluid mixture having a viscosity at 25° C. of 100 to 1,000 cst, and from 1 to 50% by weight of the cosmetic composition of cyclomethicone.

3. The composition according to claim 2 further comprising from 0.5 to 10% by weight of the cosmetic composition of a blend of cyclomethicone and dimethiconol.

4. The composition according to claim 1 further comprising from 1 to 50% by weight of the cosmetic composition of a poly ($C_2$–$C_4$ alkoxylate) polymer.

5. The composition according to claim 1 wherein the 2-methyl-1,3-propanediol is present in an amount from 1 to 70%.

6. The composition according to claim 1 wherein the 2-methyl-1,3-propanediol is present in an amount from 10 to 50%.

* * * * *